United States Patent [19]

Cookson et al.

[11] 4,177,170

[45] Dec. 4, 1979

[54] 3,3,7,8-TETRAMETHYL-2-OXABICYCLO-[4,4,0]-DECANE DERIVATIVES AND THEIR USE IN PERFUME COMPOSITIONS

[75] Inventors: Richard C. Cookson, Salisbury, England; Lorenzo D. Ferro, New York, N.Y.

[73] Assignee: Bush Boake Allen Limited, London, England

[21] Appl. No.: 916,494

[22] Filed: Jun. 19, 1978

[30] Foreign Application Priority Data

Jun. 21, 1977 [GB] United Kingdom ............ 25863/77

[51] Int. Cl.$^2$ ................................................ C11B 9/00
[52] U.S. Cl. ..................................... 252/522; 252/174; 252/174.11; 424/64; 424/69; 424/358
[58] Field of Search ...................... 252/522; 260/345.2

[56] References Cited

U.S. PATENT DOCUMENTS

| | | | |
|---|---|---|---|
| 2,483,824 | 10/1949 | Geyer et al. | 260/345.2 |
| 2,947,760 | 8/1960 | Bruin et al. | 260/345.2 |
| 3,978,090 | 8/1976 | Sanders et al. | 260/345.2 |
| 4,009,127 | 2/1977 | Ohloff et al. | 252/522 |

Primary Examiner—Veronica O'Keefe
Attorney, Agent, or Firm—Frishauf, Holtz, Goodman & Woodward

[57] ABSTRACT

Compounds having the formula:

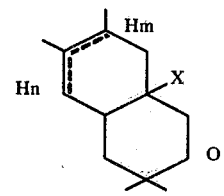

wherein X represents a hydrogen atom or an alkyl group m has a value of 0 or 1, n has a value of 1 or 2 and n+m=2 are novel. They possess unique floral odors and are useful as ingredients of compounded perfumery compositions. Especially valuable are those compounds wherein X is hydrogen and n and m have a value of one.

10 Claims, No Drawings

3,3,7,8-TETRAMETHYL-2-OXABICYCLO-[4,4,0]-DECANE DERIVATIVES AND THEIR USE IN PERFUME COMPOSITIONS

This invention is concerned with certain novel organic compounds and with perfumery compositions containing the compounds. It has been discovered that these compounds exhibit unique, attractive odours which render them useful in ingredients of perfumery compositions which compositions find use in a wide variety of applications.

From our aspect our invention provides compounds of the formula:

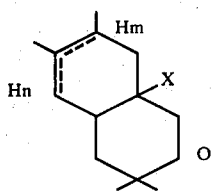

wherein X represents a hydrogen atom or an alkyl group having from 1 to 4 carbon atoms and m has a value 0 or 1, n has a value 1 or 2 and n+m=2 the dashed lines indicating alternative positions for a unit of unsaturation. Such compounds may be individual stereoisomers or mixtures of the possible stereoisomers of compounds having the above formula.

These compounds have been discovered to have a fresh floral type of odour, with a blend of prominent neroili, bitter orange notes. Furthermore, the odours of these compounds blend harmoniously with those of other known odiferous chemicals to produce useful compounded perfumery compositions.

The novel compounds of this invention are derivatives of 3,3,7,8 tetramethyl-2-oxabicyclo-[4,4,0]-decane which will hereinafter be referred to for convenience as bigarade-oxides. They may be employed as a major ingredient of these compositions depending upon the desired overall odour required. In general the bigarade-oxides will constitute from 2 to 15, preferably 3 to 7 parts by weight of the composition. The perfumery compositions of this invention may find use as such or after dilution, but more usually they are added in small proportions to other materials such as space sprays or to soap cosmetic or deodorant compositions or to substrates such as fibre fabric or paper products in order to provide them with agreeable olfactory properties. Such compositions are products of commerce and they may comprise a simple or complex mixture of individual perfumery compounds.

Thus, from a second aspect our invention provides a compounded perfumery composition comprising a plurality of odiferous chemicals together with at least one compound having the formula:

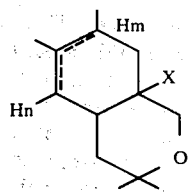

wherein X and m and n are as hereinbefore defined.

The unique fruity floral odours of the novel bigarade-oxides of our invention find special use in compositions designed for use in various perfumed bath preparations such as bath salts etc.

These novel perfumery compositions may be compounded according to recognised techniques of the perfumery arts employing known odoriferous perfumery ingredients such as those described in the standard textbooks of the art, e.g. "Soap, Perfumery and Cosmetics" by W. A. Poucher, 8th Edition, published by Chapman and Hall (London) 1974; "Perfume and Flavour Chemicals" by S. Arctander published by the author (Montclair) 1969 "Perfume and Flavour Materials of Natural Origin" also by S. Arctander self-published Elizabeth New Jersey (1960) and "Perfume Technology" by M. Billot and F. V. Wells published by Ellis Horwood Ltd. 1975. The relevant disclosures of these aforesaid textbooks are hereby incorporated by reference herein. Specific odoriferous ingredients which may be blended with the bigarade-oxides in a compounded perfumery composition are the derivatives of 2,6-dimethyl-2-alkoxy octan-7-ol (as claimed in our Dutch patent application No. 72. 15238), vetivert oil, vetiverol, vetiveryl acetate guaic wood oil, esters of anthranilic acid such as the methyl, N methyl methyl, ethyl, phenyl-ethyl, cinnamyl, linalyl, methyl and geranyl esters, benzyl acetate, lemon oil, dimethyl benzyl carbinol, dimethyl benzyl carbinyl acetate, rose absolute, jasmin absolute, ionones, iso-nonyl acetate, methyl phenyl acetate, styrallyl acetate, B. phenyl ethanol, citronellol, citronellal, hydroxy citronnelal, geranium oil, geraniol, linalol, nerol, lavandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandal-wood oil, clary sage oil, amyl salicylate, labdanum resin, methyl ionones, dihydro-myrcenol, orange oil, vanillin, ethylvanillin, olibanum resin, musk ambrette, rhodinol, mandarin oil, methylnonyl acetaldehyde, neroli oil, cedrol, oakmoss, isovalanone, eugenol, iso-eugenol, cedarwood oil, p-tert-butyl cyclohexyl acetate.

Typically the novel bigarde-oxides are blended with at least two, usually at least five and preferably at least ten of the foregoing ingredients.

Preferred compounds for present use are those wherein X represents a methyl group or a hydrogen atom. Most preferably the isomers wherein n and m have a value of 1 are used.

Particularly preferred odoriferous ingredients for blending with the bigarade-oxides are linalol, linalylacetate, bergamot oil, grapefruit oil, lemon oil, orange oil, petitgrain oil, hexycinnamic aldehyde, benzylsalicylate, methyl ionones, 2-alkoxy-2,6 dimethyl-octan-7-ols, methylanthranilate, geraniol and nerol and esters thereof, neroli oil, farnesol, nerolidol, eugenol, isoeugenol, patchouli oil, vetiveryl acetate, cedryl acetate, p-tertiary butyl cyclohexyl acetate and terpineol.

The novel bigarade-oxides may conveniently be made by a multi-step synthesis which uses the triene known as allo ocimene as its starting material. Allo acimene is readily available as a product of the thermal isomerisation of ocimene, a triene found as a constituent of several essential oils or more usually from the thermal isomerisation of a pinene.

As a first step in this synthesis allo-ocimene is reacted with an unsaturated dienophile having the formula: $CH_2=CXY$ the reaction being an example of a Diels-Alder addition. The reaction proceeds according to the following equation:

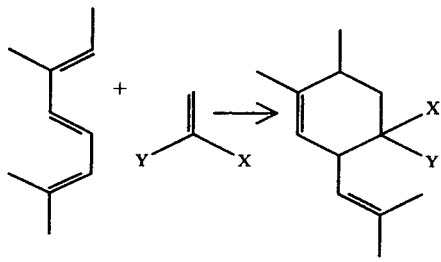

The desired intermediate for the production of the novel compounds of the invention is the compound of formula:

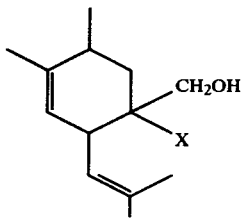

which can be produced directly by using an unsaturated alcohol as the dienophile in the above reaction, e.g. where X represents a hydrogen atom allyl alcohol can be used. Other dienophiles which yield adducts which can be converted to an alcohol having the above formula may also be employed and the nature of the substituent Y will vary accordingly. Thus acrolein, acrylic acid, acrylate esters and acrylic acid chloride can be employed. Preferably an unsaturated aldehyde is employed as the dienophile because of its properties as a dienophile and the ease with which the adduct aldehyde can be converted to the desired alcohol intermediate. Thus in this case of the preferred compounds where X represents a hydrogen atom acrolein is added to allo-ocimene. The Diels Alder addition can be carried out at elevated temperatures and pressures e.g. 120° to 180° C. and 50 to 150 psi or at ambient temperatures in the presence of a suitable electrophilic catalyst such as aluminum chloride. The Diels-Alder addition of acrolein and allyl alcohol to all-ocimene has been reported in The Journal of the Chemical Soceity of Japan Volume 5 (1973 pages 1064 to 1066). This disclosure describes the addition to a mixture of trans-trans and trans-cis allo-ocimene. When using a mixture of these two stereoisomers we prefer to carry out the reaction under elevated temperatures and pressures. When the low temperature catalysed reaction is employed the trans-cis isomer reacts extremely slowly. The Diels-Alder addition is probably stereospecific and the product which is preferably separated by fractional distillation comprises a mixture of the four stereoisomeric adducts having the above formula. These adducts are then converted to the corresponding alcohols. In the preferred case the aldehydes are reduced using the conventional technique of synthetic organic chemistry. Where other dienophiles are employed in the addition step such as an unsaturated carboxylic acid, carboxylic acid ester and carboxylic acid chloride the adducts are likewise converted to the corresponding alcohols using conventional techniques.

The conversion of the aldehyde to the corresponding alcohol may conveniently be achieved using catalytic hydrogenation i.e. heating the aldehyde adduct(s) at an elevated temperature of from 150° C. to 170° C. under superatmospheric pressure say 180 to 200 psi in an atmosphere of hydrogen gas and in the presence of a suitable catalyst. Preferably the catalyst employed is copper chromite but other conventional catalysts such as nickel, copper and palladium may be employed. Alternatively the reduction can be achieved using chemical methods in particular reduction with metal hydrides such as lithium aluminum hydride or sodium borohydride which reagents are normally added to the aldehyde as a solution in ether or water respectively, the reaction proceeding smoothly at ambient temperature. In conducting this reduction care should be taken to ensure that the ethylenic units of unsaturation present in the molecule are not attacked. The alcohols may be separated from the mixture of products formed using conventional techniques e.g. fractional distillation or used directly in the next stage in the synthesis.

The alcohol thus obtained may be cyclised to the bigarade-oxide by heating preferably under reflux in the presence of a protonic acid catalyst. Conveniently an aqueous solution of a mineral acid or phosphoric acid or an organic solution of a sulphonic acid. The reaction will usually go to completion under reflux within a period of a few hours e.g. 6 to 20 hours. Preferably an aqueous acid solution is employed as the catalyst. In order to speed the reaction a relatively concentrated solution e.g. 15 to 35% by weight is preferably employed in such a quantity that the volume of the aqueous phase is at least equal to and preferably at least twice the volume of the organic phase. The use of more concentrated acid solutions gives a desirably high yield in a relatively short time e.g. 6 to 10 hours. The oil layer may be separated from the aqueous layer and fractionated to give the desired bigarade-oxide product.

The use of organic solutions of sulphonic acids e.g. para-toluene sulphonic acids in benzene or in an alkyl benzene speeds the reaction and favours the production of these novel compounds wherein n and m have a value of 1. The organic layer is preferably washed with a dilute aqueous solution of a caustic alkali and the bigarade-oxides are then separated by fractional distillation.

The product normally comprises a mixture of the various stereoisomers of compounds having the appropriate molecular formula as defined above. It will normally comprise a mixture of the compounds wherein n has a value of 1 with those wherein n has a value of 2. This mixture can be fractionated to separate those compounds having the above formula wherein n=1 from these where n=2. In the former the novel odoriferous character is more pronounced. However, the presence of the latter complements this odour in a desirable mannor and preferably this separation step is omitted. Formation of the compounds wherein n has a value of 2 is favoured by the treatment of the alcohol with acid for a longer period or by using a stronger acid.

The invention is illustrated by the following examples:

Example 1

Preparation of 1,6-dimethyl-3-isobutenyl-4-formyl cyclohexene 554 g of allo-ocimene (85% 4E, 6Z; 15% 4E, 6E) and 224 g of acrolein were placed in a stainless steel vessel which is equipped to withstand a high internal pressure at elevated temperatures. 1 gm of embanox, a polymerisation inhibitor, was added. The air in the vessel was displaced with nitrogen and the vessel was closed. The temperature was raised to 165°–170° C. and maintained in the range for 6 hours. The maximum pressure recorded was 150 psi. The reaction mixture was then distilled and a mixture of four isomeric aldehydes collected which represented a 70% yield of the desired product. The percentages of adducts were determined by GLC to be as follows:

A 4%  B 11%  C 72%  D 13%

EXAMPLE 2

Preparation of 1,6-dimethyl-3-isobutenyl-4-formylcyclohexene 408 g of allo-ocimene (85% 4E 6Z, 15% 4E 6E) and 202 g of acrolein were placed in a stainless steel vessel which is equipped to withstand a high internal pressure at elevated temperatures. 1 gm of hydroquinone, a polymerisation inhibitor, was added. The air in the vessel was displaced with nitrogen and the vessel closed. The temperature was raised to 145°–150° C. and maintained in the range for 7.5 hours. The maximum pressure recorded was 105 psi. The reaction mixture was then distilled and a mixture of four aldehydes collected which represented a 66% yield of the desired product. The percentages of adducts were A 4%, B 11%, C 74% and D 11% where the letters A, B, C, D represent the isomers denoted as such in Example 1.

EXAMPLE 3

Preparation of 1,6-dimethyl-3-isobutenyl-4-hydroxymethyl cyclohexene 443 g of the mixed aldehyde product obtained from 2 above was mixed with 5 copper chromite and shaken in an atmosphere of hydrogen at a temperature of 150° C. and a pressure of 130–150 psi. for 14 hours. The product was filtered and distilled to give a mixture of four isomeric alcohols in 85% yield.

EXAMPLE 4

Preparation of 1,6-dimethyl-3-isobutenyl-4-hydroxymethyl cyclohexene 443 g of the mixed aldehyde product obtained from 2 above was mixed with 5 g copper chromite and shaken in an atmosphere of hydrogen at a temperature of 150° C. and a pressure of 130–150 p.s.i. for 14 hours. The product was filtered and distilled to give a mixture of four isomeric alcohols in 85% yield.

EXAMPLE 5

Preparation of 3,3,7,8-tetramethyl-2-oxabicyclo-[4,4,0]dec-6en.

1500 mls of a 10% aqueous solution of phosphoric acid were added to 500 gm of the alcohol mixture obtained in (3) above and the solution refluxed gently with stirring for a period of 8 hours. The oil layer was separated and washed with dilute aqueous caustic alkali, dried over magnesium sulphate and distilled to yield the desired product.

EXAMPLE 6

Preparation of 3,3,7,8-tetramethyl-2-oxabicyclo-[4,4,0]dec-6enes and 3,3,7,8-tetramethyl-2-oxabicyclo-[4,4,0]dec-7-enes.

3000 mls of a 30% aqueous solution of phosphoric acid were added to 1160 g of the alcohol mixture obtained in 3 above and the solution refluxed gently with stirring for a period of 12 hours. The oil layer was separated and washed with dilute aqueous caustic alkali and then water. The crude product was distilled to give a 74% yield of the six possible oxide isomers.

EXAMPLE 7

Preparation of 3,3,7,8-tetramethyl-2-oxabicyclo-[4,4,0]dec-6enes and 3,3,7,8-tetramethyl-2-oxabicyclo-[4,4,0]dec-7-enes.

20 g of para-toluene sulphonic acid in 384 g of ethylbenzene were added to 384 g of the alcohol mixture obtained in 3 above and the solution was stirred at 70°–80° C. for 7.5 h. The reaction mixture was washed with dilute aqueous caustic alkali and then water. The crude product was distilled to give a 77% yield of the six possible oxide isomers.

EXAMPLE 8

A compounded perfumery composition was made up as follow (all parts by weight):

| | |
|---|---|
| Bergamot oil | 20 |
| B pinene | 100 |
| Limonene | 140 |
| Trans-ocimene | 20 |
| Linalol | 300 |
| Linalylacetate | 80 |
| Petitgrain oil | 40 |
| Terpineol | 30 |
| Geraniol | 30 |
| Nerol | 10 |
| Neryl acetate | 20 |
| Geranyl acetate | 30 |
| Nerolidol | 50 |
| Farnesol | 20 |
| Indole (10% solution in linalol) | 25 |
| Bigarade-oxide (Product of Example 3) | 80 |
| | 1000 |

We claim:
1. A compound having the formula:

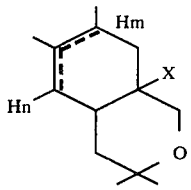

wherein X represents a hydrogen atom or an alkyl group having from 1 to 4 carbon atoms, m has a value of 0 or 1, n has a value of 1 or 2 n+m=2 and the dashed line indicates alternative positions for a unit of unsaturation.

2. A compound according to claim 1, wherein X represents a methyl group.

3. A compound according to claim 1, wherein X represents a hydrogen atom.

4. A compound according to any of the preceding claims wherein n and m each have a value of 1.

5. A compounded perfumery composition which comprises a plurality of odiferous ingredients and at least one compound having the formula 1

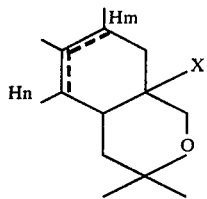

wherein X represents a hydrogen atom or an alkyl group having from 1 to 4 carbon atoms, m has a value of 0 or 1, n has a value of 1 or 2, n+m=2 and the dashed line indicates alternative positions for a unit of unsaturation.

6. A composition according to claim 5, wherein X represents a hydrogen atom.

7. A composition according to either of claims 5 or 6 wherein n and m each have a value of 1.

8. A composition according to claim 5, that the composition further comprises one or more odoriferous chemicals selected from the group consisting of linalol, linalylacetate, bergamot oil grapefruit oil, lemon oil, orange oil, petit grain oil, hexylcinnamic aldehyde, benzylsalicylate, methyl ionones, 2-alkoxy-2,6 dimethyl-octan-7-ols, methylanthranilate, geraniol and nerol and esters thereof, neroli oil, famesol, nerolidol, eugenol, isoeugenol, patchouli oil, vetiveryl acetate, cedryl acetate, p tertiary butyl cyclohexyl acetate and terpineol.

9. A composition according to claim 8 wherein the compounds of formula 1 comprise from 2 to 15 parts by weight thereof.

10. A composition according to claim 9 wherein the compounds of formula 1 comprise from 3 to 7 part by weight thereof.

* * * * *